US009714931B2

(12) United States Patent
Prabhu et al.

(10) Patent No.: US 9,714,931 B2
(45) Date of Patent: Jul. 25, 2017

(54) SYSTEM AND METHOD FOR ESTIMATING ENGINE OIL HEALTH

(71) Applicant: General Electric Company, Schenectady, NY (US)

(72) Inventors: Rahul Srinivas Prabhu, Bangalore (IN); Saratchandra Shanmukh, Bangalore (IN); Venkatesh Kattigari Madyastha, Bangalore (IN); Subramani Adhiachari, Bangalore (IN); Sethuraman Vijay, Bangalore (IN); Partho Kayal, Bangalore (IN)

(73) Assignee: General Electric Company, Niskayuna, NY (US)

( * ) Notice: Subject to any disclaimer, the term of this patent is extended or adjusted under 35 U.S.C. 154(b) by 328 days.

(21) Appl. No.: 14/476,378

(22) Filed: Sep. 3, 2014

(65) Prior Publication Data
US 2016/0061805 A1 Mar. 3, 2016

(51) Int. Cl.
*G01M 15/00* (2006.01)
*G01N 33/28* (2006.01)
*G01N 33/30* (2006.01)

(52) U.S. Cl.
CPC ..... *G01N 33/2888* (2013.01); *G01N 33/2817* (2013.01); *G01N 33/30* (2013.01)

(58) Field of Classification Search
CPC ............... G01N 33/2888; F01M 11/10; F01M 2011/14; F02D 41/0025; Y02T 10/36
USPC ...................................................... 73/114.55
See application file for complete search history.

(56) References Cited

U.S. PATENT DOCUMENTS

| | | | |
|---|---|---|---|
| 4,506,337 A | 3/1985 | Yasuhara | |
| 4,635,473 A * | 1/1987 | Hochstein | G01N 27/06 73/114.55 |
| 4,677,847 A | 7/1987 | Sawatari et al. | |
| 4,764,258 A | 8/1988 | Kauffman | |
| 4,796,204 A * | 1/1989 | Inoue | F01M 11/10 123/196 S |
| 4,839,831 A * | 6/1989 | Imajo | F01M 11/10 123/196 S |
| 5,750,887 A * | 5/1998 | Schricker | F01M 11/10 340/438 |
| 5,987,976 A | 11/1999 | Sarangapani | |
| 6,082,322 A | 7/2000 | Graham et al. | |
| 6,253,601 B1 * | 7/2001 | Wang | F01M 11/10 340/438 |

(Continued)

*Primary Examiner* — Eric S McCall
*Assistant Examiner* — Mohammed E Keramet-Amircola
(74) *Attorney, Agent, or Firm* — Pabitra K. Chakrabarti

(57) ABSTRACT

A system includes a sensor that may measure one or more engine oil parameters to assess engine oil health of an engine and a processor communicatively coupled to the sensor and that may receive a signal from the sensor. The signal is representative of a real-time measurement of the one or more engine oil parameters. The processor may also estimate the one or more engine oil parameters over time via an adaptive predictive model associated with the one or more engine oil parameters to generate estimated data and reconcile the real-time measurement and the estimated data to generate an integrated engine oil degradation model and predict engine oil remaining useful life based on the integrated engine oil degradation model and one or more condemn limits associated with the one or more engine oil parameters.

22 Claims, 5 Drawing Sheets

(56) References Cited

U.S. PATENT DOCUMENTS

| | | | | |
|---|---|---|---|---|
| 6,327,900 B1* | 12/2001 | McDonald | F01M 1/18 | 701/29.5 |
| 6,449,538 B1* | 9/2002 | Kubo | F01M 11/10 | 701/29.5 |
| 6,580,366 B1* | 6/2003 | Engfehr | G01N 33/2805 | 340/438 |
| 6,920,779 B2 | 7/2005 | Carlstrom et al. | | |
| 7,521,945 B2 | 4/2009 | Hedges et al. | | |
| 7,581,434 B1* | 9/2009 | Discenzo | G01N 33/2888 | 73/53.01 |
| 8,087,287 B2 | 1/2012 | Cummings | | |
| 2002/0129645 A1* | 9/2002 | Konno | F01M 1/18 | 73/114.57 |
| 2003/0146050 A1* | 8/2003 | Dayal | F01M 1/18 | 184/1.5 |
| 2005/0039521 A1* | 2/2005 | Han | F01M 11/10 | 73/53.05 |
| 2008/0127711 A1* | 6/2008 | Farag | B25B 23/1425 | 73/1.11 |
| 2008/0250851 A1* | 10/2008 | Keller | F01M 11/12 | 73/114.55 |
| 2009/0192728 A1* | 7/2009 | Wright | G01N 33/2888 | 702/33 |
| 2009/0217740 A1* | 9/2009 | Nedachi | F01M 11/10 | 73/54.01 |
| 2009/0306875 A1* | 12/2009 | Jiang | F02D 35/023 | 701/102 |
| 2010/0122571 A1* | 5/2010 | Han | F01M 11/10 | 73/54.01 |
| 2010/0281971 A1* | 11/2010 | Beneker | F01M 11/10 | 73/290 R |
| 2010/0307230 A1* | 12/2010 | Gilch | G01N 33/2888 | 73/114.55 |
| 2011/0320138 A1* | 12/2011 | Rajagopalan | F01D 21/003 | 702/34 |
| 2014/0119889 A1* | 5/2014 | Prabhu | G01M 5/0083 | 415/118 |
| 2015/0075268 A1* | 3/2015 | Qi | G01N 27/22 | 73/114.55 |
| 2015/0192560 A1* | 7/2015 | Basu | G01N 33/2888 | 73/114.55 |

* cited by examiner

SYSTEM AND METHOD FOR ESTIMATING ENGINE OIL HEALTH

BACKGROUND

The subject matter disclosed herein relates to evaluation of engine lubrication, and more specifically to systems and methods for determining remaining useful life of engine oil.

Rail transport vehicles (e.g., locomotives) may undergo periodic maintenance to continue functioning efficiently with high reliability and comply with environmental standards. Generally, the locomotives are serviced after certain predetermined periods of usage (e.g., at 92 day intervals), or time in service (e.g., after engine run times of 26,000 Megawatt Hours (MWH)) to ensure safe operation of locomotives. During periods of routine maintenance, engine oil and filters are drained or changed every 92 or 184 days. In addition, frequent engine oil samples are collected approximately every 10 to 15 days and sent to off-site laboratories for analysis and assessment of engine oil health. However, routine maintenance based on predetermined periods of usage or time in service may result in premature drainage of healthy engine oil (e.g., engine oil in good condition), thereby increasing operational costs of the locomotives (e.g., materials, equipment, maintenance resources, etc.). In addition, sending engine oil samples off-site for analysis may result in time delays, data inconsistencies, and added costs (e.g., processing and handling fees).

BRIEF DESCRIPTION

Certain embodiments commensurate in scope with the originally claimed invention are summarized below. These embodiments are not intended to limit the scope of the claimed invention, but rather these embodiments are intended only to provide a brief summary of possible forms of the invention. Indeed, the invention may encompass a variety of forms that may be similar to or different from the embodiments set forth below.

In a first embodiment, a system includes a sensor that may measure one or more engine oil parameters to assess engine oil health of an engine and a processor communicatively coupled to the sensor and that may receive a signal from the sensor. The signal is representative of a real-time measurement of the one or more engine oil parameters. The processor may also estimate the one or more engine oil parameters over time via an adaptive predictive model associated with the one or more engine oil parameters to generate estimated data and reconcile the real-time measurement and the estimated data to generate an integrated engine oil degradation model and predict engine oil remaining useful life based on the integrated engine oil degradation model and one or more condemn limits associated with the one or more engine oil parameters.

In a second embodiment, a system includes a processor including one or more tangible, non-transitory, machine-readable media collectively storing one or more sets of code and one or more processing devices that may execute the one or more sets of code to predict health of engine oil associated with an engine. The one or more sets of code include instructions for receiving a signal from a sensor. The signal is representative of a real-time measurement of the one or more engine oil parameters. The one or more sets of code also include instructions for modeling each of the one or more engine oil parameters over time based on engine operational parameters, reconciling the real-time measurement with the respective model data for each of the one or more engine oil parameters, and predicting the health of the engine oil based on an adaptive integrated engine oil degradation model and condemn limits for each of the one or more engine oil parameters.

In a third embodiment, a method includes measuring a plurality of engine oil parameters associated with engine oil health with one or more sensors that may measure an engine oil sample, transmitting sensed data from the one or more sensors to a processor communicatively coupled to the one or more sensors, modeling each of the plurality of engine oil parameters based on an operational parameter of an engine associated with the engine oil sample to generate model data, reconciling the sensed data with the respective model data for each of the plurality of engine oil parameters, and predicting a condition of the engine oil sample based on predetermined limits for each of the plurality of engine oil parameters.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
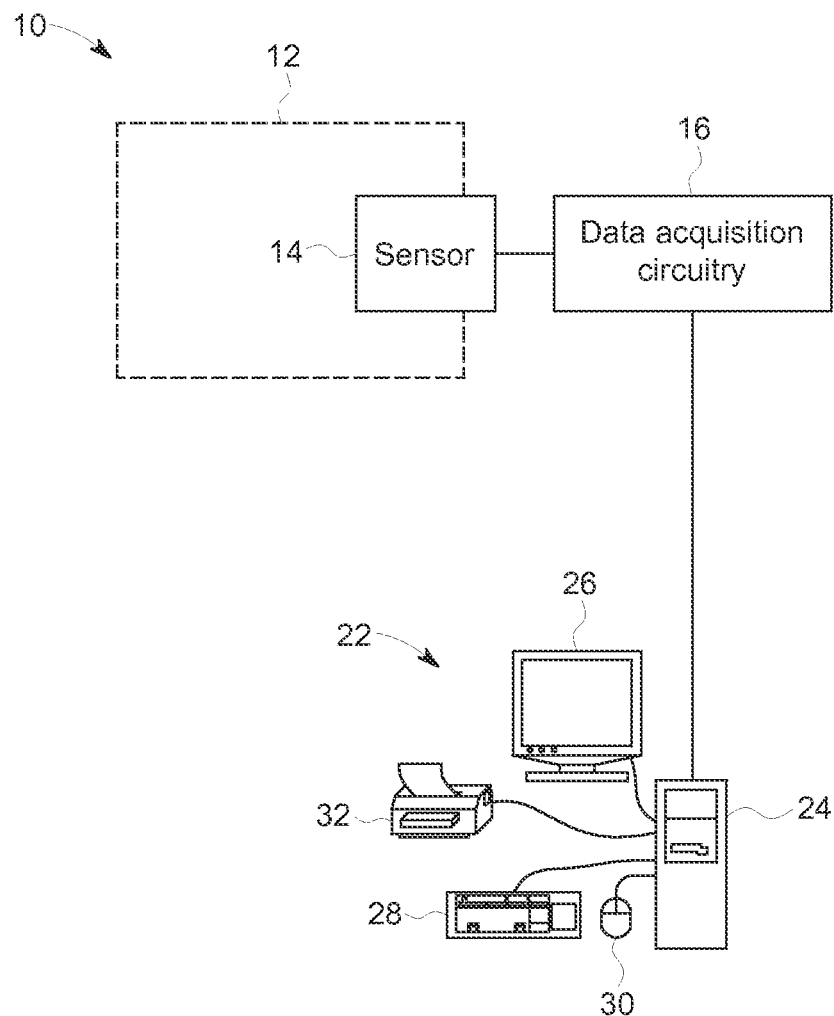
FIG. 1 is a block diagram of a system for assessing engine oil health, in accordance with an embodiment of the disclosure.

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

Rail transport vehicles (e.g., locomotives) undergo periodic servicing based on predetermined periods of usage or time in service to evaluate engine health and compliance with environmental standards. However, servicing locomotives based on predetermined maintenance periods may result in unnecessary servicing for locomotives having good engine health (e.g., draining and replacing good engine oil). In addition, locomotives exhibiting good engine health during one routine maintenance period may develop poor engine health prior to the next routine maintenance period. Release of unreliable locomotives from a servicing station may be attributed to inconsistencies in data quality and limitations associated with on-site (e.g., at the servicing station) evaluation of engine oil health before release of the locomotives from the servicing station. For example, it may not be practical to set up equipment generally used to assess engine oil health, such as inductively coupled plasma (ICP) and total gravimetric analysis (TGA) instruments, due to space limitations, and the environment at the servicing station may be unsuitable for operation of certain equipment. In addition, analysis of engine oil samples via ICP and TGA may be time consuming. Therefore, the use of off-site testing facilities may cause time delays in receiving the engine oil data and the locomotives are released from the servicing station prior to assessing engine oil health. As such, current assessment of engine oil health may increase the overall operational costs of locomotives due to unnecessary drainage of good engine oil at predetermined periods and/or decreased locomotive reliability.

Accordingly, it may be desirable to monitor locomotive engine health on-site during routine maintenance schedules and predict engine oil health (e.g., oil degradation and remaining useful life) to minimize unnecessary drainage of good engine oil at predetermined periods and release of unreliable locomotives (e.g., locomotives having poor engine health) from servicing stations. This may be achieved by evaluating key engine oil parameters during routine maintenance of the locomotives using field sensors and modeling the key engine oil parameters to estimate the engine oil health based on real-time sensor measurements and operational conditions of the locomotive engine. Therefore, provided herein is an integrated model-based technique that uses both the real-time sensor measurements and model data for field monitoring of engine oil health and prediction of engine oil remaining useful life. While the present embodiments are discussed with regard to locomotive engine oil health, it should be appreciated that the system and methods disclosed herein may also be applied to other engines and/or vehicles (e.g., heavy duty trucks, aircrafts, automobiles, marine vessels, etc.).

To facilitate discussion of the disclosed embodiments, reference will be made to engine oil. However, the system and methods disclosed herein may also be used for analysis of any other fluid of interest, such as, but not limited to, one or more fuels (e.g., oil, gasoline, diesel fuel, jet fuel, etc.), gear oil, hydraulic fluid, lubricating oils, etc., organic and/or vegetable oils, bio-fuels, petrodiesel-biodiesel fuel blends, etc., as well as synthetic based lubricants. Turning now to the drawings, and referring first to FIG. 1, an embodiment of a model based system 10 used for monitoring and estimating engine oil health is illustrated as including a fluid reservoir 12 for engine oil and one or more sensors 14. The one or more sensors 14 may be disposed in or on the reservoir 12 or may be coupled to in-line connectors in fluid communication with the fluid reservoir 12. In certain embodiments, the one or more sensors 14 may be configured to provide continuous or intermittent monitoring of the engine oil within the reservoir 12.

The one or more sensors 14 are configured to sense chemical properties (e.g., alkalinity, oxidation, nitration, etc.) and physical properties (e.g., viscosity) of the engine oil. Additionally, the one or more sensors 14 may facilitate evaluation of engine oil contaminants due to fuel and/or water leakage and wear metals that may be indicative of the overall operating condition of the locomotive. By way of example, the one or more sensors 14 may include optical sensors, flow sensors, viscosity sensors, resonant sensors, or any other suitable sensor, or combinations thereof. In certain embodiments, the one or more sensors 14 may utilize techniques such as, but not limited to, infrared (IR) spectroscopy and flow viscometry (e.g., Hele Shaw flow viscometry), or any other suitable technique, or combinations thereof to evaluate chemical and physical properties of the locomotive engine oil. In addition, the one or more sensors 14 may be part of a hand-held field device or stationary equipment located at the servicing station such as the Spectro-Q3000, Spectroil, and Spectro-Fluidscan available from Spectro Scientific.

Data from the one or more sensors 14 may be acquired via data acquisition circuitry 16, which may be associated with the one or more sensors 14 or with a control system, such as a monitor or workstation 22 including data processing circuitry, where additional processing and analysis may be performed. The data acquisition circuitry 16 can be within the fluid reservoir 12 or can be within the workstation 22. The data acquisition circuitry 16 may be in the form of a sensor reader, which may be configured to communicate wirelessly with the fluid reservoir 12 and/or the workstation 22. For example, the sensor reader may be a battery-operated device.

In addition to displaying the data, the operator workstation 22 may control the above-described operations and functions of the system 10. The operator workstation 22 may include a processor 24 having one or more processor-based components, such as general purpose or application specific computers. In addition to the processor-based components, the processor 24 may include various modules or subsystems (e.g., software systems implemented as computer executable instructions stored in a non-transitory machine readable medium such as memory, a hard disk drive, or other short term and/or long term storage) that may be used to estimate engine oil degradation and forecast remaining useful life (RUL) for the sampled engine oil. The memory may be used for storing programs and routines (e.g., code or instructions) for performing the techniques described herein that are executed by the operator workstation 22 or by associated components of the system 10.

Alternatively, the programs and routines may be stored on a computer accessible storage and/or memory remote from the operator workstation 22, but accessible by network and/or communication interfaces present on the processor 24. When the programs and routines are transferred or provided over a network or other communications connection (either hardwired, wireless, or a combination of hardwired or wireless) to a machine, the machine properly views the connection as a machine-readable medium. Thus, any such connection is properly termed a machine-readable medium. The machine-readable medium may include machine-executable instructions and data which cause a processor, such as the processors 24, or any general purpose computer, special purpose computer, or special purpose processing machines to perform a certain function or group of functions. As discussed below, the processor 24 may execute instructions or code contained on the machine-readable or computer-readable storage medium and generates one or more outputs, as discussed in more detail below.

The processor 24 may also include various input/output (I/O) interfaces, as well as various network or communication interfaces. The various I/O interfaces may allow communication with user interface devices, such as a display 26, keyboard 28, mouse 30, and printer 32, that may be used for viewing and inputting configuration information and/or for operating the system 10. The various network and communication interfaces may allow connection to both local and wide area intranets and storage networks as well as the Internet. The various I/O and communication interfaces may utilize wires, lines, or suitable wireless interfaces, as appropriate or desired.

The one or more sensors 14 may each include an integrated circuit memory chip that may contain different types of information associated with a type of sensor 14. Non-limiting examples of such information in the memory of the integrated circuit chip include calibration coefficients for the sensor, sensor lot number, production date, end-user information, and any other suitable information. The information stored in the integrated circuit memory chip may be utilized by the processor 24 to calculate and/or estimate engine oil health parameters. For example, in certain embodiments, the system 10 may predict and/or forecast engine oil health based on data obtained from the one or more sensors 14 and a mathematical oil degradation model, as will be described in further detail below. That is, the processor 24 may combine both real-time sensor measurements with model computed parameters to estimate engine oil health. In this way, the degradation of the engine oil may be estimated and RUL of the engine oil may be predicted at a suitable confidence interval.

Figure 2:
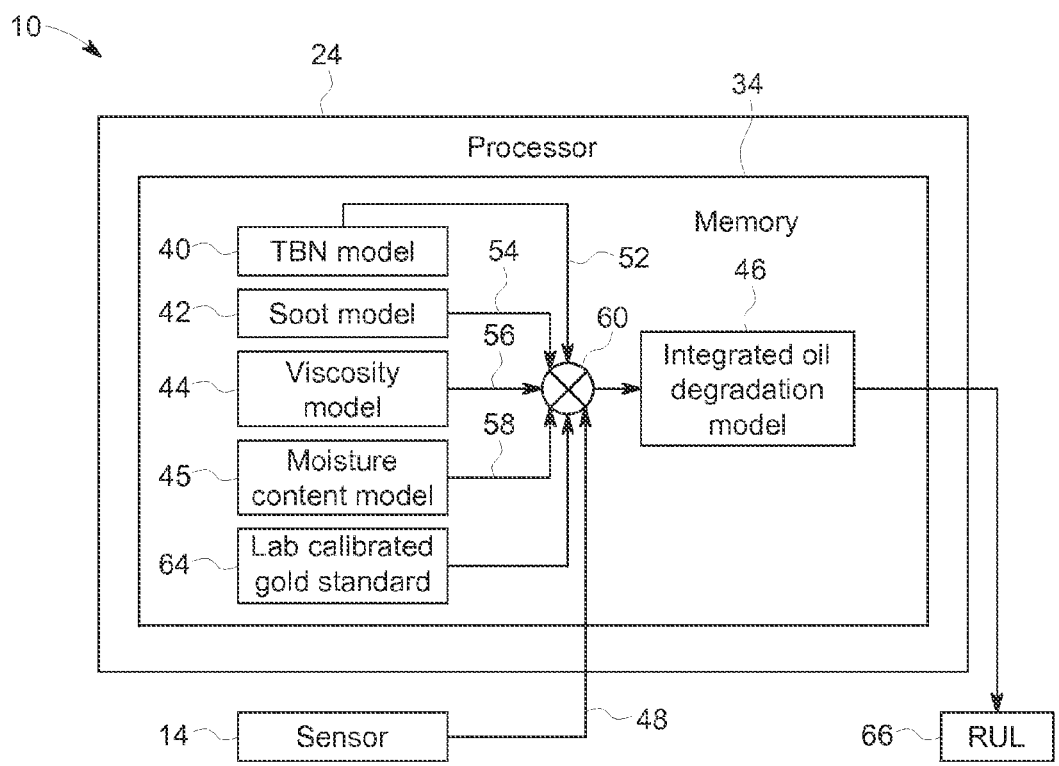
FIG. 2 is a block diagram of the system of FIG. 1 including a model-based processor, in accordance with an embodiment of the disclosure.

As discussed above, the system 10 may be used for on-site evaluation of engine oil health and predicting RUL of the engine oil for locomotives undergoing routine maintenance at the servicing station. Accordingly, the processor 24 may be configured to generate and implement a variety of control models that estimate key engine oil parameters based on inputs associated with operational conditions of the locomotives (e.g., engine duty cycles, engine revolutions per minute (RPM), and/or engine load information) to model and estimate engine oil degradation over time. FIG. 2 illustrates an embodiment of the system 10 configured to model engine oil degradation and predict RUL of the engine oil sample. The system 10 includes a memory 34 that may store information used to determine engine oil parameters (e.g., TBN, soot loading, viscosity, moisture, etc.) and predict RUL. For example, the memory 34 may store one or more physics-based models (e.g., FIGS. 5 and 6), calibration standards, condemn limits, and any other information that may be used by the processor 24 to estimate key engine oil parameters. In the illustrated embodiment, the memory 34 is disposed within the processor 24. However, in other embodiments, the memory 34 may be located in the one or more sensors 14 or other external device accessible by the processor 24 via a network and/or communication interface, as discussed above.

In certain embodiments, the memory 34 stores a total base number (TBN) model 40 (e.g., an oxidation model) for computing depletion of TBN in the engine oil sample, a soot model 42 (e.g., Talbot model) for computing accumulation of soot (e.g., soot loading), a viscosity model 44 (e.g., Orrick and Erbar model), and a moisture content model 45 (e.g., polynomial regression). The models 40, 42, 44, and 45 may be integrated into an integrated oil degradation model 46 that may be used to predict the RUL of the engine oil sample at the servicing station and determine if engine oil drainage is necessary during the scheduled maintenance. As discussed in further detail below, in certain embodiments the integrated oil degradation model 46 is a self-adaptive model. That is, the integrated oil degradation model 46 may adapt to different types of engine oils (e.g., engine oil grades). In certain embodiments, the memory 34 may store coefficient tables, constants (e.g., kinetic constants of base oils or anti-oxidants, soot factor), viscosity bias, or any other information that may be utilized to estimate the TBN, soot loading, moisture content, and viscosity of the engine oil sample with the models 40, 42, 44, and 45. The coefficients may be periodically updated (e.g., manually or automatically) to reduce any effects of model uncertainty on the estimated engine oil parameters. The memory 34, or other suitable storage components, may include magnetic and optical mass storage devices, internal memory, such as RAM chips. As should be appreciated, the system 10 may include additional models that may facilitate evaluation and estimation of engine oil health parameters.

The processor 24 may receive information from external sources to facilitate forecasting of engine oil health (e.g., RUL). Accordingly, the processor 24 is communicatively coupled (e.g., wired or wireless connection) to the one or more sensors 14 such that the processor 24 may receive and store (e.g., in the memory 34) sensed data 48 from the one or more sensors 14. In this way, the processor 24 may utilized the sensed data 48 and the data computed from the models, such as TBN output 52, soot output 54, viscosity output 56, and moisture content output 58 to estimate the engine oil health (e.g., oil degradation). The processor 24 may analyze the model data and the sensed data 48 using algorithms that fuse (e.g., reconcile) the sensed data 48 and model data (e.g., outputs 52, 54, 56, and 58) to estimate engine oil degradation and predict RUL within a suitable confidence interval. For example, the memory 34 may include instructions that apply a Kalman filter 60 (e.g., a linear quadratic estimation model) that reconciles the TBN output 52, the soot output 54, the viscosity output 56, and the moisture content output 58 with the respective sensed data 48. In embodiments in which the sensed data 48 and the model data are biased and noisy (e.g., due to inaccuracy of the measurement or estimation, operator error, environmental conditions, etc.), the model and sensor data are fused in the Kalman filter 60. As should be noted, Kalman filter derivatives such as, iterative and non-iterative extended Kalman filters (EKF) and unextended Kalman filters (UKF). In certain embodiments, the model and sensor data may be fused in a particle filter (PF). Accordingly, the Kalman filter 60 may include a set of mathematical equations (e.g., sub-models) and computations that utilized calibration standards 64 (e.g., benchmark values/"gold" standard) to efficiently and accurately estimate engine oil degradation. The Kalman filter 60 may estimate kinetic constants, soot factors, and viscosity bias, based on reconciled input data (e.g., sensor data 48 and model outputs 52, 54, 56, and 58) to correct the sensor data 48 and model outputs 52, 54, 56, and 58. The corrected data may be used as inputs in the integrated oil degradation model 46, thereby improving the forecast accuracy for the RUL of the engine oil. Accordingly, the system 10 may utilize sensors that may be prone to bias and drift errors. In addition, the system 10 may accommodate varying sampling rates for different sensors, and thereby accommodate for delayed arrival of sensor values (e.g., the sensor data 48).

In certain embodiments, the integrated oil degradation model 46 is self-adaptive. For example, during initial analysis of the engine oil sample, the integrated oil degradation model 46 may provide predictions on engine oil RUL with a limited amount of information from sensor 14 (e.g., the sensor data 48). That is, RUL predictions may be mainly based on the model outputs 52, 54, 56, and 58. However, as the sensor 14 collects more sensor data 48, the integrated oil degradation model 46 may adapt to type of engine oil (e.g., engine oil grade) being analyzed. As such, the integrated oil degradation model 46 may correct the RUL prediction based on correction coefficients for the engine oil grade of the engine oil sample, and thereby accurately predict RUL 66. Therefore, the system 10 is robust to a variety of engine oil grades and allows for self-tuning of the engine oil grade and additive factors with limited availability of information from the sensor 14. Accordingly, prediction of the RUL 66 for engine oil samples using the system 10 is independent of engine oil grade and geographical location of the locomotive servicing stations.

In certain embodiments, the Kalman filter 60 may include a Kalman filter gain matrix (KFGM), which may be an array of numbers representing the uncertainty weighted sensitivity models of estimated parameters (e.g., the model outputs 52, 54, and 56) to changes in model performance multipliers. The Kalman filter 60 may use supplied inputs (e.g., the sensed data 48, the models 40, 42, 44, and 45, the model outputs 52, 54, 56, and 58, and/or the calibration standards 64) to generate performance multipliers that are applied to estimate bias drift and tune (e.g., validate) the models 52, 54, 56, and 58. For example, in one embodiment, the Kalman filter 60 may fuse the viscosity model 44 and the sensed data 48 associated with temperature, dynamic viscosity, and density of the engine oil sample to estimate the bias drift for engine oil viscosity. The calibration standards 64 associated with engine oil viscosity may be used to validate the bias drift estimation. The calibration standards 64 may include reference data generated from standard wet chemistry methods (e.g., inductively coupled plasma (ICP), total gravimetric analysis (TGA), titration, etc.), generally used to analyze engine oil health at off-site testing facilities. In certain embodiments, the Kalman filter 60 may use the integrated oil degradation model 46 as an input to the models 40, 42, 44, and 45 to tune the models 40, 42, 44, and 45, and thereby increase accuracy of the model outputs 52, 54, 56, and 58.

Once the bias drift for each respective model (e.g., models 40, 42, 44, and 45) and sensed data (e.g., the sensed data 48) has been estimated, the processor 24 may tune the models 40, 42, 44, and 45 to predict a RUL 66 of the engine oil with a suitable degree of accuracy and confidence interval. The data from the three different sources (e.g., the one or more sensors 14, the models 40, 42, 44, or 45, and the calibration standards 64) may be triangulated (e.g., reconciled) in the Kalman filter 60 to generate the integrated oil degradation model 42 (e.g., an empirical/regression model) that may be used to derive a reliable estimation for the RUL 66 based on predetermined condemnation limits for each measured/estimated engine oil parameter (e.g., TBN, soot, viscosity, moisture, etc.). Additional inputs associated with the operational conditions of the engine (e.g., engine duty cycle, engine RPM, engine loading, etc.) may be provided to the integrated oil degradation model 46 to derive the RUL 66. In this way, additional oil quality sensors may not be necessary for estimating engine oil degradation within a suitable confidence interval.

Figure 3:
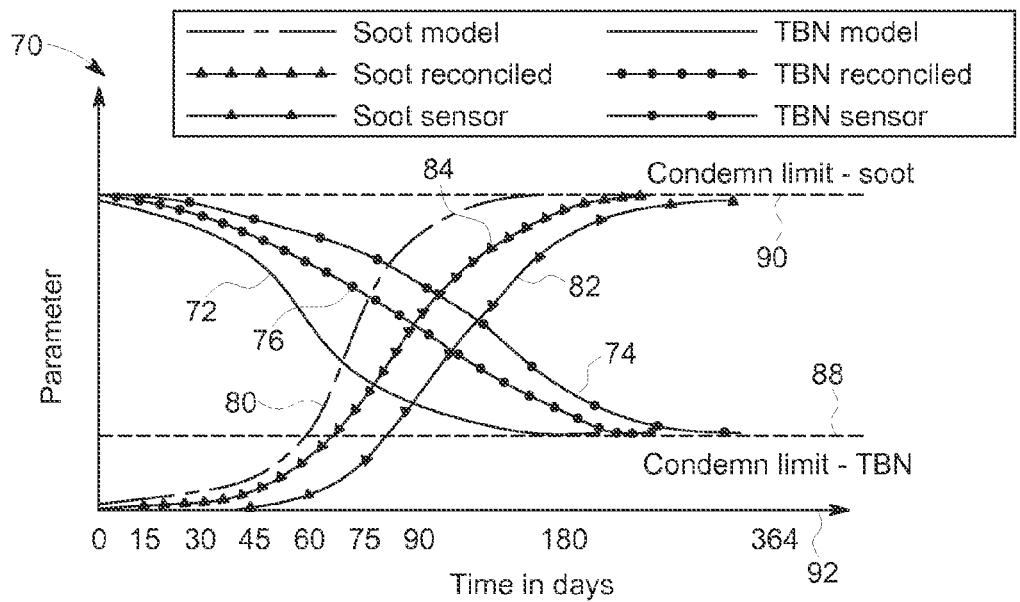
FIG. 3 is a graph of measured, modeled, and reconciled engine oil parameters, in accordance with an embodiment of the disclosure.

FIG. 3 depicts a graph 70 for engine oil RUL derived from three distinct data sets (e.g., sensor, model, and filter) for each respective engine oil parameter (e.g., TBN, soot loading, viscosity, moisture content) being evaluated. To facilitate discussion of the graph 70, reference will only be made to engine oil parameters associated with TBN and soot loading. However, additional engine oil parameters may be considered in such analyses. In the illustrated embodiment, the graph 70 includes TBN sensor data 72, TBN model data 74, and TBN reconciled data 76 and soot sensor data 80, soot model data 82, and soot reconciled data 84. In addition, the graph 70 includes TBN condemn limit 88 and soot condemn limit 90 that provide boundaries for TBN and soot loading associated with good engine oil health. As discussed above, the integrated oil degradation model 46 utilizes pre-determined condemn limits, such as TBN and soot condemn limits 88 and 90, respectively, to predict the RUL of the engine oil. The three distinct data sets for each engine oil parameter evaluated are plotted over time 92 to estimate the remaining useful life of the engine oil and determine when it may be desirable to drain the engine oil form the locomotive. As illustrated in graph 70, the reconciled data 76 and 84 (e.g., fused sensor and model data) calculated in the Kalman filter 60 is between the sensed and model data, thereby indicating that a true value for each engine oil parameter (e.g., TBN, soot loading, viscosity, moisture, etc.) is somewhere in between the sensed data (e.g., the sensor data 72 and 80) and the model data (e.g., model data 74 and 82). Therefore, by utilizing the reconciled data 76 and 84, in conjunction with condemn limits 88 and 90, respectively, the integrated oil degradation model 46 may predict RUL for the engine oil sample (e.g., via regression analysis by the Kalman filter 60) with a suitable accuracy and confidence interval. The estimates derived from the integrated oil degradation model 46 at each time interval may be used to periodically correct the model prediction (e.g., the RUL 66) and tune the models 40, 42, 44, and 45. In one embodiment, the RUL 66 may be corrected between approximately every 7 to 15 days. In other embodiments, the predicted oil RUL may be corrected between approximately every 15 to 30 days. As should be noted, the calibration standards 64 may also be used to periodically calibrate the one or more sensors 14 to further improve the accuracy of the RUL 66.

In addition to the inputs from the one or more sensors 14 and the models 40, 42, 44, and 45, the integrate oil degradation model 46 may receive inputs associated with engine operation parameters, such as engine duty cycle, engine RPM, and locomotive load information to facilitate predicting engine oil degradation with high accuracy. The integrated oil degradation model 46 may predict oil degradation and RUL with data associated with a composition of the engine oil sample (e.g., TBN, soot, viscosity, moisture, etc.) and fault/wear parameters of the locomotive (e.g., engine RPMs and load). Therefore, additional oil quality sensors may not be necessary, and thereby reducing the amount of on-site equipment and/or analysis of the engine oil sample at off-site testing facilities. In addition, the integrated oil degradation model 46 may predict RUL 66 independent of engine configurations. For example, the integrated oil degradation model 46 may be used to predict RUL 66 for engine oil sampled from engine configurations with and without exhaust gas recirculation (EGR) and without additional knowledge of the engine's lubrication system design. Furthermore, because the integrated oil degradation model 46 is dependent on engine oil composition and not engine configuration, the integrated oil degradation model 46 may be used to predict RUL of used and new engine oil sample.

As discussed above, by reconciling the sensed data 48, the models 40, 42, and 44, and the calibration standards 64 in the Kalman filter 60, the processor 24 may generate an estimate of oil health data and the RUL 66 of the engine oil with high accuracy. Accordingly, based on the RUL 66, personnel at the servicing station may determine whether the engine oil may need to be drained/discarded or topped-off (e.g., add engine oil to the engine) to maintain a desired volume of engine oil in the engine of the locomotive during the routine maintenance irrespective of the predetermined period for oil change based on usage or time in service of the locomotive. For example, if the reconciled data (e.g., reconciled data 76 and 84) for at least one of the engine oil parameters is outside a desired range (e.g., the condemn limits 88 and 90), the processor 24 may indicate to a user that the engine oil may need to be drained and replaced. Conversely, if each of the engine oil parameters are within the desired range, the processor may indicate good engine oil health, and thereby the engine oil may not be drained and replaced during the routine maintenance. Rather, a volume of engine oil may be added to the locomotive to top-off the engine oil. In certain embodiments, the processor 24 may indicate an amount (e.g., volume) of engine oil that may need to be added to the engine to maintain a desired engine oil level. This may reduce unnecessary drainage of engine oil, the release of unreliable locomotives from the servicing station, and dependence on off-site testing facilities. As such, the overall operational cost of the locomotives may be decreased.

In addition to measuring TBN, soot loading, viscosity, and moisture content, the system 10 may also measure additional parameters that may be indicative of engine oil health. For example, in certain embodiments, the system 10 may measure glycol, sulfation, nitration, and oxidation levels of the engine oil sample. The system 10 may also perform elemental analysis of the engine oil sample. As such, the system 10 may measure levels of silver (Ag), aluminum (Al), boron (B), barium (Ba), calcium (Ca), cadmium (Cd), chromium (Cr), copper (Cu), iron (Fe), manganese (Mn), molybdenum (Mo), nickel (Ni), phosphorous (P), silicon (Si), and tin (Sn) in the engine oil sample. As such, the system 10 may facilitate diagnostic testing of locomotives at the servicing station without the use of additional equipment.

Figure 4:
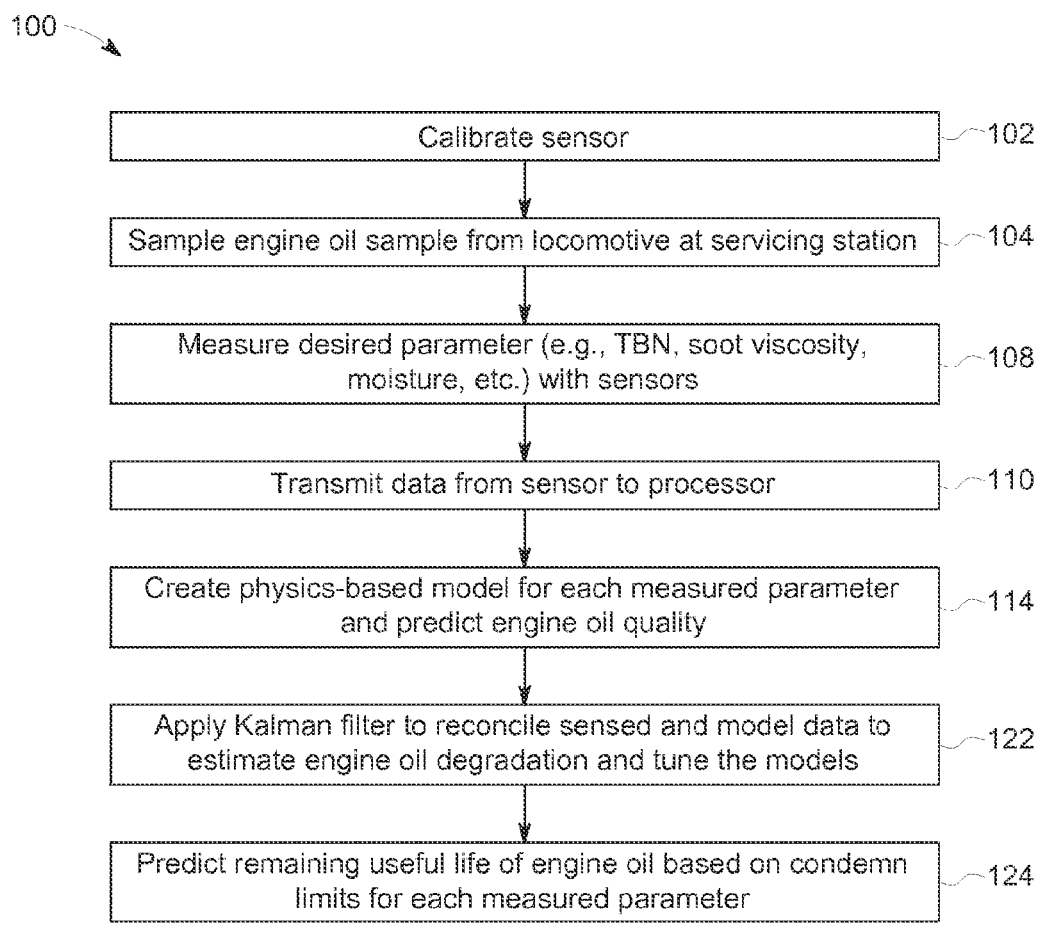
FIG. 4 is a method for predicting the remaining useful life of the engine oil, in accordance with an embodiment of the disclosure.

Present embodiments also include a method that may be implemented by the system 10 to evaluate engine oil health. FIG. 4 illustrates a flow diagram of a method 100 by which the system 10 estimates engine oil degradation and predicts the RUL of the engine oil sample. The method includes calibrating the one or more sensors 14 (block 102) and sampling engine oil from the locomotive, or any other desired engine, at the servicing station (block 104). This is generally done during routine maintenance of the locomotive. The method also includes measuring one or more engine oil parameters (e.g., TBN, soot loading, viscosity, moisture, etc.) with one or more sensors, e.g., the one or more sensors 14 (block 108) and transmitting the sensed data to a processor, e.g., the processor 24 (block 110). As discussed above, evaluation of key engine oil parameters associated with chemical and physical characteristics of the engine oil may provide information about engine oil health. As such, measuring compositional components of the engine oil may facilitate estimating engine oil degradation and predicting the RUL for the engine oil sampled.

Figure 5:
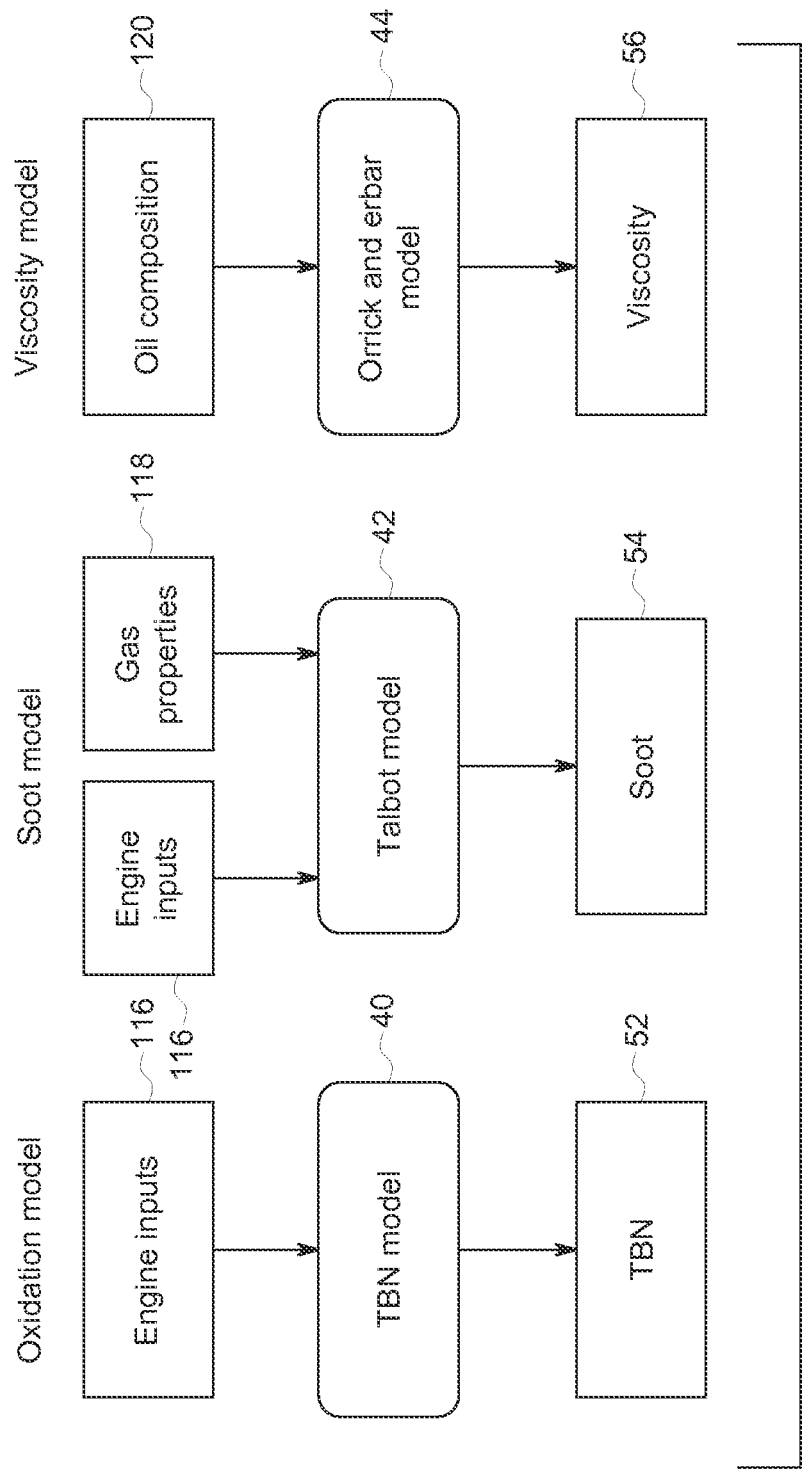
FIG. 5 is a block diagram of engine oil parameter models used for estimating engine oil total base number, soot loading, and viscosity in accordance with an embodiment of the disclosure.

The method further includes modeling the engine oil quality over time using a physics-based model for each engine oil parameter measured, e.g., the models 40, 42, and 44 (block 114). The models 40, 42, and 44 estimate the key engine oil parameters (e.g., TBN, soot loading, viscosity, moisture content, etc.) to assess the engine oil quality over time based on inputs from the one or more sensors (e.g., the sensed data 48) and operational parameters associated with the engine, such as engine duty cycle, engine RPM, and engine loading. As illustrated in FIG. 5, the models 40, 42, 44, and 45 may receive inputs associated with the engine oil sample (e.g., engine oil composition, density, thickness, temperature, etc.), gas properties, and engine inputs (e.g., engine operational parameters and engine geometry). For example, the TBN model 40 may receive engine parameter inputs 116, the soot model 42 may receive the engine parameter inputs 116 and locomotive gas properties 118, and the viscosity model 44 may receive engine oil composition parameters 120. The inputs may be measured, obtained from tables stored in the memory 34, or a combination thereof. In addition, the models 40, 42, 44, and 45 may be used to assess engine oil levels and determine oil top-up volumes.

Figure 6:
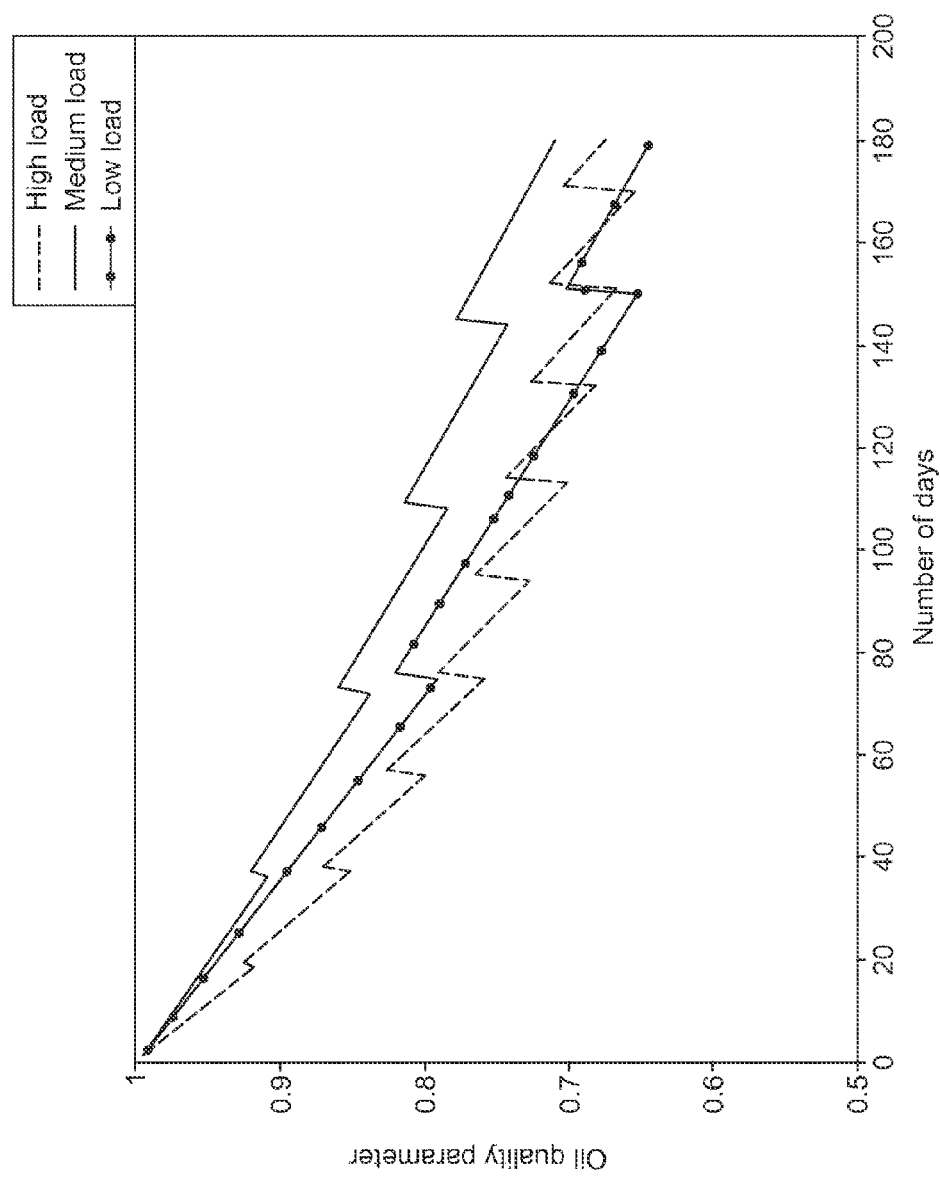
FIG. 6 is a plot of estimated engine oil quality as a function of time based on an engine oil parameter model, in accordance with an embodiment of the disclosure.

FIG. 6 is a graph providing a representative example of an engine oil quality parameter output obtained from one of the models 40, 42, 44, or 45 as a function of time (e.g., the number of days in service) for locomotives running at a given load (e.g., megawatt hours (Mwh)). As expected, the engine oil quality parameter decreases over time based on the locomotive load. For example, locomotives operating at a high load exhibit reduced engine oil quality over time compared to locomotives operating at medium and low loads. Accordingly, high load locomotives may need to have the engine oil topped-up more frequently. For example, in certain embodiments, high load locomotives may need to have the engine oil topped-up between approximately 4 to approximately 8 times more during a period of approximately 180 days compared to medium and low load locomotives. Therefore, based on the model output for the one or more engine oil parameters, an operator may assess whether the engine oil may need to be topped-up during servicing. Additionally, the model output may be used to determine a volume of engine oil that may be needed to top-up the locomotive. This information may also facilitate in optimizing engine-oil top-up and/or engine oil replacement schedules. Because the model 40, 42, 44, and 45 receive the sensor data 48, the models may accurately predict engine oil top-up and replacement. As used herein, high load locomotives generally operate at greater than 60% of a normal Mwh operation, medium load locomotives generally operate at between approximately 40% to approximately 60% of the normal Mwh operation, and low load locomotives operate at between approximately 20% and approximately 40% of the normal Mwh operation.

Returning to FIG. 4, the method also includes applying a Kalman filter (e.g., the Kalman filter 60) to the sensed data 48 and the model-based estimates (e.g., model outputs 52, 54, and 56) to reconcile (e.g., fuse) the sensed data 48 with the model data and estimate engine oil degradation using the integrated oil degradation model 46 and tune the models 40, 42, 44, and 46 (block 122). The Kalman filter 60 uses the calibration standards 64 to validate the models 40, 42, and 44 by estimating the bias drift between the sensor data 48 and the model outputs 52, 54, and 56. In this way, the engine oil parameters (e.g., TBN, soot loading, viscosity, moisture content, etc.) may be estimated at a suitable accuracy and confidence interval. As such, the processor 24 may also forecast the RUL 66 based on condemn limits for each of the engine oil parameters within a suitable confidence interval (block 124).

Technical effects of the invention include techniques for evaluating several key engine oil parameters, such as TBN, soot loading, viscosity, and moisture content, to predict the RUL of the engine oil on-site (e.g., at the servicing station) during schedule routine maintenance of locomotives. The techniques use a Kalman filter to reconcile data from one or more sensors and physics-based models that are associated with a respective key engine oil parameter. With the use of calibration standards and condemn limits for each engine oil parameter, the RUL may be predicted with improved accuracy at the servicing station. As such, the engine oil may not need to be replaced at predetermined times, thereby reducing the overall operational and maintenance costs for locomotives.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A system, comprising:
   a sensor configured to measure one or more engine oil parameters to assess engine oil health of an engine; and
   a processor communicatively coupled to the sensor and configured to:
      receive a signal from the sensor, wherein the signal is representative of a real-time measurement of the one or more engine oil parameters;
      estimate the one or more engine oil parameters over time via an adaptive predictive model associated with the one or more engine oil parameters to generate estimated data;
      reconcile the real-time measurement and the estimated data to generate an integrated engine oil degradation model and predict engine oil remaining useful life based on the integrated engine oil degradation model and one or more condemn limits associated with the one or more engine oil parameters,
   wherein the adaptive predictive model self-tunes depending on engine oil grade.

2. The system of claim 1, wherein the processor comprises a tangible, non-transitory, machine-readable media storing the adaptive predictive model, the integrated engine oil degradation model, and the condemn limits.

3. The system of claim 1, wherein the processor is configured to apply a filter to reconcile the real-time measurement and the model data.

4. The system of claim 3, wherein the filter comprises a Kalman filter or a particle filter.

5. The system of claim 1, wherein the processor is configured to triangulate the real-time measurement, the estimated data, and sensor calibration data to validate the adaptive predictive model and the integrated engine oil degradation model.

6. The system of claim 1, wherein the one or more engine oil parameters comprise a total base number parameter, a soot loading parameter, a viscosity parameter, a moisture content parameter, or a combination thereof.

7. The system of claim 1, wherein the engine operational parameters comprise engine duty cycle, engine revolutions per minute, engine load, or a combination thereof.

8. The system of claim 1, wherein the processor is configured to provide the integrated engine oil degradation model as an input to the adaptive predictive model.

9. The system of claim 1, wherein the processor is configured to display an indication of the engine oil remaining useful life.

10. The system of claim 1, wherein the processor is configured to determine engine oil top-up parameters based on the estimated data.

11. A system, comprising:
    a processor, comprising:
       one or more tangible, non-transitory, machine-readable media collectively storing one or more sets of code; and
       one or more processing devices configured to execute the one or more sets of code to predict health of engine oil associated with an engine, wherein the one or more sets of code comprises instructions for:
          receiving a signal from a sensor, wherein the signal is representative of a real-time measurement of the one or more engine oil parameters;
          modeling each of the one or more engine oil parameters over time based on engine operational parameters;
          reconciling the real-time measurement with the respective model data for each of the one or more engine oil parameters; and
          predicting the health of the engine oil based on an adaptive integrated engine oil degradation model and condemn limits for each of the one or more engine oil parameters,
    wherein the adaptive integrated engine oil degradation model self-tunes depending on engine oil grade.

12. The system of claim 11, wherein the instructions are configured to apply a Kalman filter to reconcile the real-time measurement and the model data.

13. The system of claim 11, wherein the instructions are configured to apply a Kalman filter to tune the adaptive integrated engine oil degradation model.

14. The system of claim 11, wherein the engine oil parameters comprise a total base number parameter, a soot loading parameter, a viscosity parameter, and a moisture content parameter.

15. The system of claim 11, wherein the integrated engine oil model comprises a total base number model, a soot model, a viscosity model, and a moisture content model.

16. The system of claim 11, wherein the engine operational parameters comprise an engine duty cycle, engine revolutions per minute, engine loading, or a combination thereof.

17. A method, comprising:
    measuring a plurality of engine oil parameters associated with engine oil health with one or more sensors configured to measure an engine oil sample;
    transmitting sensed data from the one or more sensors to a processor communicatively coupled to the one or more sensors;
    modeling each of the plurality of engine oil parameters based on an operational parameter of an engine associated with the engine oil sample to generate model data;
    reconciling the sensed data with the respective model data for each of the plurality of engine oil parameters; and predicting a condition of the engine oil sample based on predetermined limits for each of the plurality of engine oil parameters, wherein the adaptive model of engine oil degradation adapts to a grade of the engine oil sample.

18. The method of claim 17, comprising applying a Kalman filter to reconcile the sensed data and the model data, wherein the Kalman filter is configured to tune an adaptive model of engine oil degradation.

19. The method of claim 17, wherein the condition comprises a condemn condition if at least one of the plurality of engine oil parameters is in a range that is outside the predetermined limits.

20. The method of claim 17, wherein the plurality of engine oil parameters comprise a total base number parameter, a soot loading parameter, a viscosity parameter, and a moisture parameter.

21. The method of claim 17, wherein the operational parameter comprises an engine duty cycle, engine revolutions per minute, engine loading, or a combination thereof.

22. The method of claim 17, comprising determining an oil top-up volume based on the model data.

* * * * *